United States Patent [19]
Ellman et al.

[11] Patent Number: 5,683,386
[45] Date of Patent: Nov. 4, 1997

[54] ELECTROSURGICAL ELECTRODE FOR NAIL SPICULE REMOVAL PROCEDURE

[76] Inventors: Alan G. Ellman; Jon C. Garito, both of 1135 Railroad Ave., Hewlett, N.Y. 11557

[21] Appl. No.: 560,640

[22] Filed: Nov. 20, 1995

[51] Int. Cl.$^6$ .................................................. A61B 17/39
[52] U.S. Cl. .................................. 606/41; 606/49
[58] Field of Search .................. 606/41, 45, 49, 606/50

[56] References Cited

U.S. PATENT DOCUMENTS

| | | | |
|---|---|---|---|
| 4,103,688 | 8/1978 | Edwards | 606/49 |
| 4,269,174 | 5/1981 | Adair | 606/49 |
| 4,517,975 | 5/1985 | Garito et al. | |
| 5,195,959 | 3/1993 | Smith | 606/49 |

OTHER PUBLICATIONS

Brunelle et al, "A Bipolar Electrode . . . " Radiology, vol. 137, No. 1, pp. 239–240, Oct. 1980.

Primary Examiner—Lee S. Cohen

[57] ABSTRACT

An electrode for use in an electrosurgical procedure for excising nail spicule tissue. In a preferred embodiment, the electrode is characterized by a bare active dome-shaped tip portion. The undesired tissue excising is effected with the bare tip and the adjacent portions of the electrode shaft are made insulating to prevent accidental burns to the patient and to allow the physician to use these insulated parts to help position and guide the active tip portion during the surgical procedure.

13 Claims, 2 Drawing Sheets

ELECTROSURGICAL ELECTRODE FOR NAIL SPICULE REMOVAL PROCEDURE

This invention relates to an electrosurgical electrode for electrosurgically treating the growth of a symptomatic spicule in the nail groove of a patient.

BACKGROUND OF THE INVENTION

In our prior U.S. Pat. No. 4,517,975, whose contents are incorporated herein by reference, we describe the configuration of an electrosurgical electrode for use in a surgical procedure for the destruction of the nail matrix in a patient, sometimes referred to as a nail matrisectomy procedure. The common name for the ailment is ingrown nail. The electrosurgical electrode designed for this purpose has a thin flat spade-shaped bare working end at the tip of an insulated shank. One side of the spade-shaped working end is insulated so that only the uncoated bare side is capable of supplying high frequency currents. In operation, the electrode is inserted under the tissue fold covering the nail plate edge and electrosurgical currents supplied to destroy tissue cells adjacent the bare side of the electrode.

A problem arises when a symptomatic spicule grows in the corner of the nail deep in the cul-de-sac matrix tissue in the proximal groove. The spicule, which is a small spike-shaped bone or bone fragment, can grow at the very deepest part of the tunnel in the cul-de-sac, which makes it difficult to reach with the flat spade-shaped electrode described in the referenced patent.

Other known treatments, such as chemical, cryo, or laser treatments, typically cause great pain, produce recurrent episodes of ingrown nails, discomfort, and disability.

SUMMARY OF THE INVENTION

An object of the invention is an improved surgical procedure for the removal of symptomatic spicule growth in the nail groove of a patient.

Another object of the invention is an improved electrosurgical electrode for the electrosurgical treatment of ingrown nail.

We have invented a novel electrode for use in an electrosurgical nail spicule removal procedure. This electrosurgical procedure using our novel electrode enables physicians to offer to patients a treatment that is efficiently performed, easily learned by the physician and thus performed at a significantly reduced price, and with less tissue damage and superior results compared to non-electrosurgical procedures.

The procedure using our novel electrode is based on matrix destruction deep in the cul-de-sac in the nail groove. The electrode of the invention is uniquely configured to enable the active tip to reach and electrosurgically destroy the undesired spicule growth by advancing the electrode proximally into the groove until it reaches the spicule, whereupon energizing the electrode will destroy the nail spicule with at most minimal damage to the surrounding tissue.

In a preferred embodiment, our novel electrode is characterized by a bare active dome-shaped tip portion extending from a completely insulated shank portion of the electrode. The active tip portion is configured to fit deep within the cul-de-sac to reach the spicule growth. The spicule destruction is effected without it being necessary for the bare tip to be moved by the surgeon, and the adjacent portions of the tip support and electrode shaft are made insulating to prevent accidental burns to the patient and to allow the physician to use these insulated pads to help position and guide the active tip portion during the surgical procedure. The electrosurgical procedure has the important advantages of being able to destroy the undesired tissue while at the same time coagulating the adjacent tissue causing minimum bleeding. It is preferred that the electrosurgical currents used be above 1.5 MHz, and preferably above 3 MHz. At these high frequencies, commonly referred to as radiosurgery, destruction is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
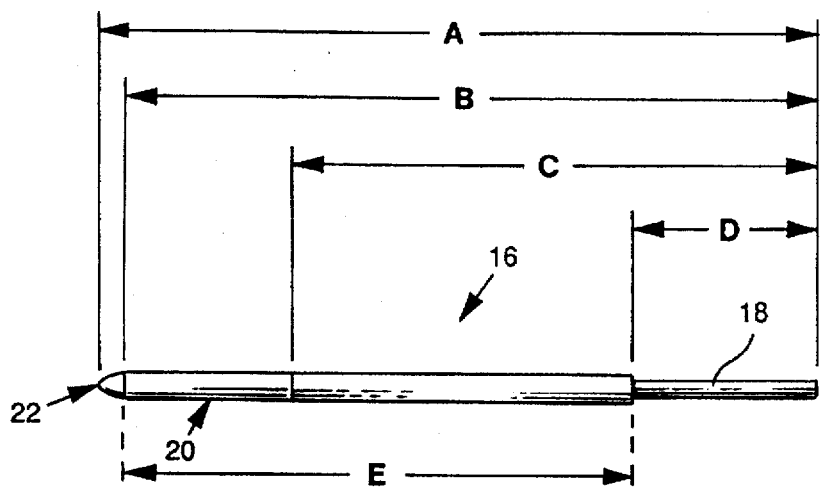
FIG. 1 is a side view of one form of electrosurgical electrode in accordance with the invention prior to provision of electrically-insulating coatings.
Figure 2:
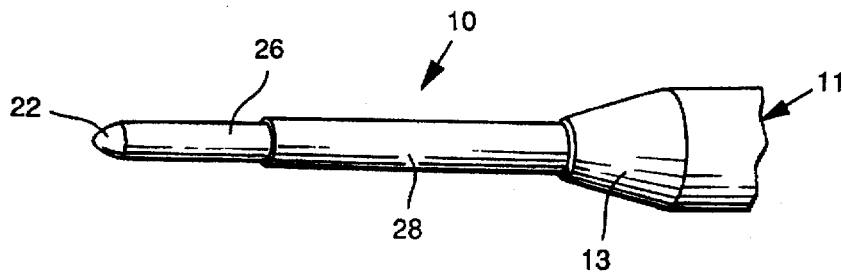
FIG. 2 is a perspective view of the completed electrode of FIG. 1 shown mounted in a conventional electrosurgical handpiece.
Figure 3:
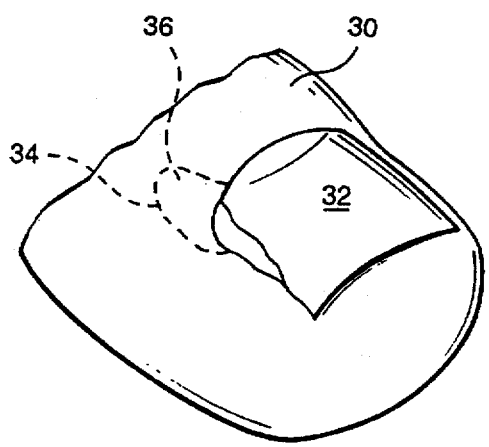
FIG. 3 is a perspective view of the end of the large toe of a typical patient showing the nail groove.
Figure 4:
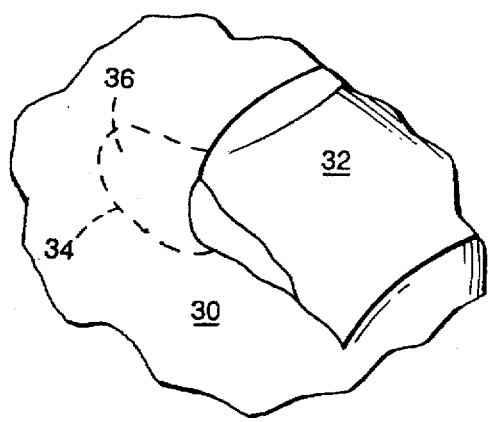
FIG. 4 is an enlarged view of just the nail groove of FIG. 3.
Figure 5:
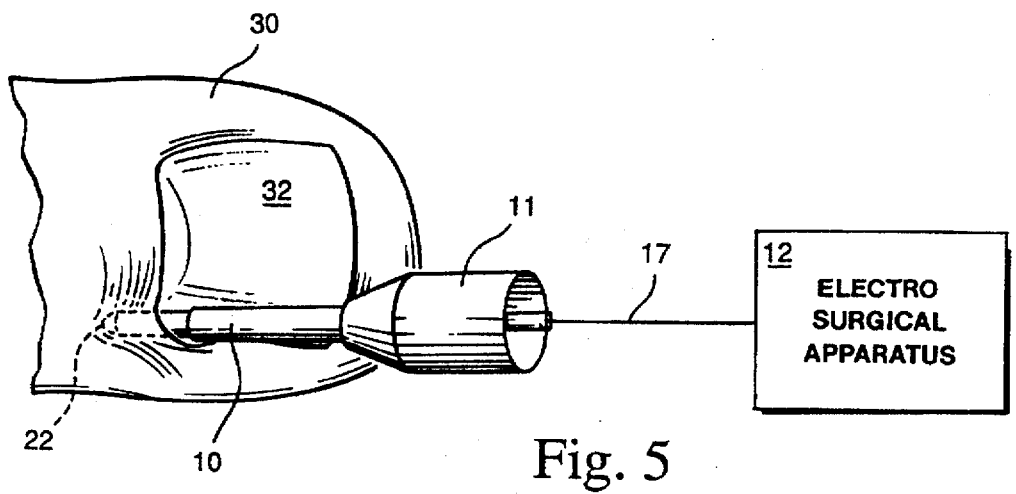
FIGS. 5 and 6 are perspective views showing how the electrode of FIG. 2 is used in a surgical procedure in accordance with the invention.

FIGS. 1 and 2 illustrates a preferred form of the novel electrosurgical electrode 10 of the invention mounted in a standard handpiece 11 (only the front end of which is shown) which is connected in the conventional manner to conventional electrosurgical apparatus 12 as illustrated in FIG. 5. As an example only, and not meant to be limiting, the handpiece can be a model H6 Surgitron handpiece available from Ellman International, Inc. of Hewlett, N.Y. and the electrosurgical apparatus can be model AAOP Surgitron FFPF available from the same supplier. The Ellman equipment is preferred due to its high operating frequency, typically at 3.8 MHz. Such handpieces 11 conventionally comprise an electrically insulating pen-like member 13 having an electrically conductive tube (not shown) running lengthwise through it and configured to receive the bare metal shaft of the electrosurgical electrode 10. Not shown are the conventional collet type fittings at the handpiece front end to hold the metal shaft in position and to establish the desired electrical connection thereto. The opposite end of the electrically conductive tube is connected by way of a cable 17 to the electrosurgical apparatus 12. Also connected to the latter is the usual indifferent plate (not shown) which during use is in contact with the patient's body. When the electrosurgical apparatus is energized, high frequency electrosurgical currents are generated which are coupled by way of the electrically conductive tube of the handpiece to the electrode 10. The physician, in the usual way, holds the handpiece while applying the working end of the electrode to the desired area of the patient to be treated.

In accordance with the present invention, as illustrated in FIGS. 1 and 2, the electrosurgical electrode comprises a straight shaft 16, for example, of brass, having at one end, the right end, a bare portion 18 to provide a good electrical connection to the handpiece, and at the opposite or working end a bare dome-shaped or bevelled tip 22 serving as the active electrode portion. The shaft 16 is constituted preferably of a thin brass rod, and the active tip 22, which is also solid metal, which may be a continuation of the shaft or is brazed or welded to the shaft end. The active tip 22 is electrically connected to the shaft 16 and any electrosurgical currents conveyed to the shaft are in turn available at the active tip 22. FIG. 1 shows the shape of the electrode 10 during an intermediate step in its manufacture when it is constituted solely of metal.

A preferred embodiment has the following dimensions in inches, indicated in FIG. 1 by the letters A–D: A=2.65; B=2.55; C=2.0; D=0.7. These dimensions are not critical except for the shape and size of the dome-shaped tip 22, and that the diameter of the finished shank should not exceed the diameter of the dome-shaped tip at its widest part or base. The shank diameter is chosen to have a conventional diameter to fit the standard handpiece, such as 0.063 inches. In the FIG. 1 illustration, the entire structure is bare. Preferably but not essentially, the shaft portion is divided into a slightly smaller section 18 at the right end and a slightly larger middle section forming a shoulder 24 which can conveniently act as a stop when the electrode is inserted into the handpiece. A more significant dimension is the diameter of the base of the dome-shaped tip 22, as this part extends deeply into the proximal nail groove. A preferred diameter is about 0.094 inches, with a suitable range of about 0.08–0.11 inches. The dome-shaped tip portion 22 preferably has a length in the axial direction of about 0.1 inches, and can range from about 0.08–0.2 inches in length.

In accordance with a further feature of the invention, the portion indicated by 20 extending from the shoulder 24 adjacent its free end 18 adjacent the handpiece 11, to the active dome-shaped tip 22 close to but spaced from its end, referenced E, is covered with a coating of an electrically-insulating material, which may be one of many suitable electrically-insulating plastics. Preferably, during subsequent manufacturing steps, the area indicated by 20 is coated with a thin electrically-insulating coating 26, baked Teflon being one example. The insulation extends to the shoulder 24, but from the point where the thin electrically-insulating coating 26 ends to the shoulder 24, a less expensive thicker electrically-insulating coating may be used, such as a rubber tube 28, provided on the metal shank 16 by a conventional heat shrink process so as to overlap the adjacent edge of the thin coating 26.

The reasons for the electrode shape and protective coatings will be clearer from a description of one form of the surgical procedure with reference to FIGS. 3–6, which show a schematic view of a typical large toe 30 of a patient with a nail 32. Another structural feature is the proximal nail groove 34 terminating in a cul-de-sac 36 at the deepest part of the tunnel formed by the nail groove 34. The cul-de-sac 36 forms a common region for the growth of a nail spicule. It is this region 36 that is difficult to reach with the electrode described in the referenced patent.

Figure 6:
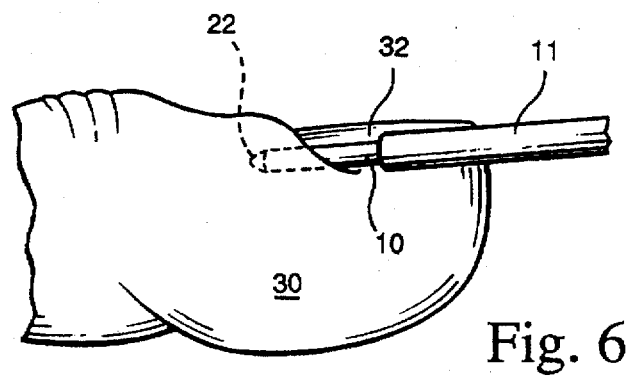

The procedure for achieving matrix destruction of any undesired spicule in the cul-de-sac 36 is relatively simple with the novel electrode 10 of the invention. The surgeon extends the handpiece-held electrode 10 through the nail groove passageway proximally as shown in FIGS. 5 and 6 until the dome-shaped tip 22 is positioned deep into the cul-de-sac 36, and then turns on the electrosurgical apparatus 12. The electrosurgical currents emanating from the rounded bare dome-shaped tip 22 will achieve matrix destruction only in the cul-de-sac region 36. An important advantage of removal electrosurgically of the spicule is simultaneous coagulation of any cut blood vessels which minimizes bleeding and trauma.

The shape of the electrode 10, with a generally long, axially-oriented, main portion, makes it relatively easy to insert the electrode and reach the cul-de-sac region desired. The insulating coatings 26, 28 are essential to prevent accidental burning or other tissue damage by the sides of the electrode as the instrument is manipulated through the nail groove passageway. Also, the inactive parts of the electrode 10 can be used by the physician to help position the active tip 22 exactly where it is needed.

Figure 7:
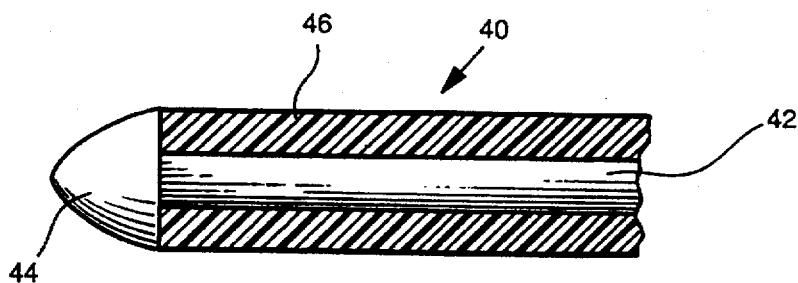
FIGS. 7 and 8 are side views of different active end portions of electrodes in accordance with the invention.
Figure 8:
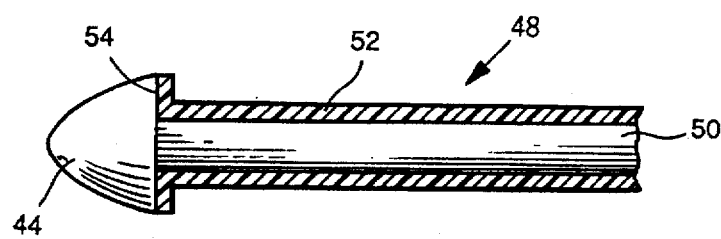

The preferred electrode embodiment of FIG. 2 comprised a shank diameter of the portion 20 of the same size as that of the widest base part of the dome-shaped tip 22. FIG. 7 shows a modified shape of electrode 40 comprising a thinner shank 42 terminating in a wider dome-shaped tip 44, with the thinner shank coated with a thicker electrically-insulating coating 46 so that the resultant diameter is about the same as that of the dome-shaped tip 44. FIG. 8 shows a further modification employing a wider shank 50 with the same dome-shaped tip 44 and with a thinner insulating coating 52 so that the overall diameter is smaller than that of the dome-shaped tip 44. In this instance, the electrically-insulating coating 52 also has to extend over the rear side 54 of the dome-shaped tip so it too is prevented from discharging electrosurgical currents in undesired areas.

With the Ellman equipment, the fully rectified or cut/coag current is used at a power setting of about 3–4 with the active bare tip electrode 22. There is very little trauma and any soreness in the toe felt by the patient is easily handled by analgesia and anti-inflammatory drugs.

The procedure described can be effective in reducing the effects of ingrown nail and offers the advantages of avoiding the use of expensive lasers or other treatments, and much patient trauma post-surgery. The procedure is effective not only for treatment of the growth of a symptomatic spicule in the nail groove, but can also be used in instances of previously incomplete matrisectomy due to poor technique or cul-de-sac matrix tissue not reachable by other methods.

It will also be understood that the electrode of the invention is not limited to its use for treating nail spicules. To those skilled in this art, there will certainly be other uses for this novel electrode that provides an active dome-shaped tip arranged in-line to the shaft, with the adjacent electrode sections coated with insulating material for accurately guiding and controlling the position of the active tip during a tissue excising electrosurgical procedure.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for nail spicule treatment, comprising:

(a) an electrically-conductive shaft having a first end for receiving electrosurgical currents and a second end, (b) said second end having a portion terminating in an active, electrically-conductive, dome-shaped, tip portion, the active tip portion having a diameter at the base of the dome of approximately 0.1 inches, (c) said active tip portion being exposed electrically for applying electrosurgical currents when said shaft is connected to a source of electrosurgical currents, (d) said active tip portion being configured to allow a physician to advance the active tip portion proximally in the groove at the corner of a patient's toe nail to reach the vicinity of a symptomatic spicule in the nail groove, (e) portions of said shaft adjacent said active tip portion being electrically-insulating to prevent contact and passage of electrosurgical currents to adjacent or surrounding tissues.

2. The electrosurgical electrode as claimed in claim 1, wherein the active tip portion extends substantially in-line with the shaft.

3. An electrosurgical electrode as claimed in claim 2, wherein the active tip portion has a length from the base of the dome to its tip of approximately 0.1 inches.

4. An electrosurgical electrode as claimed in claim 3, wherein the portions of the shaft between its first end and the location of the junction at the beginning of the active tip portion are coated with an electrically insulating coating.

5. An electrosurgical electrode as claimed in claim 2, wherein the active tip portion has a diameter at the base of the dome approximately equal to the diameter of the shaft.

6. An electrosurgical electrode as claimed in claim 2, wherein the active tip portion has a diameter at the base of the dome substantially larger than the diameter of the shaft.

7. An electrosurgical electrode as claimed in claim 1, wherein the shaft is coated with a first electrically-insulating coating from the vicinity of its exposed first end to a point spaced from the active tip portion, and the shaft is coated with a second electrically-insulating coating that is thinner than the thickness of the first coating from the point where the first coating ends to the active tip portion.

8. An electrosurgical electrode as claimed in claim 1, wherein the shaft is tubular and of metal, and the active tip portion is of solid metal.

9. An electrosurgical electrode as claimed in claim 1, wherein the length of the active tip portion is in the range of about 0.08–0.2 inches in length.

10. In combination:

electrosurgical apparatus capable of supplying high frequency currents, an electrosurgical handpiece having means at one end connected to the electrosurgical apparatus and having at its opposite end means for holding the electrically conductive shaft of an electrosurgical electrode and for supplying the high frequency currents to said electrode;

an electrosurgical electrode for performing nail spicule removal, comprising:

(a) an electrically conductive shaft member having a first end for mounting at the opposite end of the handpiece for receiving high frequency currents and a second end, (b) said second end having a portion terminating in an active, electrically conductive, tip portion, (c) said active tip portion being generally dome-shaped and having a diameter in the range of about 0.08–0.11 inches and being exposed electrically for applying high frequency currents when said electrosurgical apparatus is energized, (d) said active tip portion being configured to allow a physician to advance the active tip portion proximally in the groove at the corner of a patient's toe nail to reach the vicinity of a symptomatic spicule in the nail groove, (e) portions of said shaft member adjacent said active tip portion being electrically insulating to prevent contact and passage of high frequency currents to adjacent or surrounding tissues.

11. The combination as claimed in claim 10, wherein the length of the active tip portion is in the range of about 0.08–0.2 inches.

12. The combination of claim 10, wherein the high frequency currents are at a frequency exceeding 1.5 MHz.

13. A surgical procedure for removing a nail spicule from the toe of a patient, comprising the steps:

(a) providing electrosurgical apparatus connected to a handpiece holding an electrosurgical electrode, said electrosurgical electrode, comprising:

(i) an electrically conductive shaft member having a first end for receiving electrosurgical currents and a second end, (ii) said second end having a portion terminating in an active, electrically conductive, tip portion, (iii) said active tip portion being generally dome-shaped and exposed electrically for applying electrosurgical currents when said shaft member is connected to a source of electrosurgical currents, (iv) said active tip portion being configured to allow a physician to advance the active tip portion proximally in the groove at the corner of a patient's toe nail to reach the vicinity of a symptomatic spicule in the nail groove, (v) portions of said shall member adjacent said active tip portion being electrically insulating to prevent contact and passage of electrosurgical currents to adjacent or surrounding tissues, (b) advancing the electrode proximally into the corner of the nail groove until the active tip portion reaches the spicule growth at the cul-de-sac end, and (c) activating the electrosurgical apparatus until the spicule tissue is destroyed.

* * * * *